United States Patent [19]
Franklin

[11] Patent Number: 5,326,353
[45] Date of Patent: Jul. 5, 1994

[54] LEG PROSTHESIS DEVICE HAVING HINGE ASSEMBLY FOR KNEELING

[76] Inventor: James D. Franklin, 110 Zimmerman Dr., Providence, Ky. 42450

[21] Appl. No.: 987,658

[22] Filed: Dec. 9, 1992

[51] Int. Cl.⁵ .............................................. A61F 2/64
[52] U.S. Cl. ........................................ 623/39; 602/16
[58] Field of Search ............................ 602/16; 16/374; 623/40–46, 39

[56] References Cited

U.S. PATENT DOCUMENTS

| | | | |
|---|---|---|---|
| 927,973 | 7/1909 | Jepson | 16/374 X |
| 1,228,257 | 5/1917 | Stuck | 16/374 X |
| 1,258,710 | 3/1918 | Rowley | 623/39 |
| 1,375,860 | 4/1921 | Rowley | 623/46 X |
| 1,409,414 | 3/1922 | Rowley | 623/44 X |
| 1,447,230 | 3/1923 | Winn | 623/43 |
| 1,914,882 | 6/1933 | Caron | 623/39 |
| 2,542,567 | 2/1951 | Peters | 623/45 |
| 2,794,987 | 6/1957 | Oliver | 623/43 |
| 3,643,755 | 2/1972 | Gionet et al. | 16/374 X |
| 4,614,181 | 9/1986 | Karlsson | 602/16 |
| 4,726,362 | 2/1988 | Nelson | 602/16 X |
| 4,727,861 | 3/1988 | Yeomans et al. | 623/39 X |

FOREIGN PATENT DOCUMENTS

| | | | |
|---|---|---|---|
| 0200720 | 11/1958 | Austria | 623/39 |
| 1137344 | 9/1962 | Fed. Rep. of Germany | 16/374 |
| 0638323 | 4/1962 | Italy | 16/374 |

*Primary Examiner*—Randall L. Green
*Assistant Examiner*—D. Willse
*Attorney, Agent, or Firm*—Camoriano & Smith

[57] ABSTRACT

A leg prothesis device for use as an upper leg prothesis permitting the wearer of the device to kneel thereupon comprising a first member adapted to support an upper leg prosthesis and a second member spaced from the first member adapted to support a lower leg portion connected to a foot prothesis. The first and second members are movable with respect to each other between a maximum leg angle of about 180° and a minimum leg angle of about 20°. A connecting member connecting the first and second members comprises three arm portions: (1) a curved portion pivotally connected at one distal end to the first member and defining a pivot axis between the first and second members; (2) a first linear portion that is integral with the curved portion; and (3) a second linear portion angularly connected to the first linear portion. The second linear portion is fixedly connected to said second member with the curved portion being pivotably connected to the first member at a point located intermediate a vertical extension of the second linear portion and a vertical axis of the second member when the leg angle is about 180°. The first member is provided with a slot through which the first linear portion extends and moves.

10 Claims, 2 Drawing Sheets

LEG PROSTHESIS DEVICE HAVING HINGE ASSEMBLY FOR KNEELING

Technical Field.

This invention relates to a prosthetic device, particularly to an above-knee prosthetic device having a hinge assembly permitting kneeling on the device by the user.

BACKGROUND OF THE PRESENT INVENTION

Prosthetic devices for above-knee applications generally are found in two forms: devices that attach by a belt and harness arrangement generally about the pelvic area and devices that attach to the stump by suction. Both suffer from the infirmity that neither are particularly useful to the many wearers whose work and life styles require considerable kneeling and moving about on the knees. Typical prior art prosthetic devices do not permit constant kneeling and moving about due to the delicate nature of the devices and the inability thereof to bend the knee assembly at an angle sufficient to permit the crawling about on the prosthetic knee. Conventionally to kneel with many prior art prosthetic devices, the wearer must thrust one leg in front for stability and to kneel on the other, assuming the device will rotate sufficiently. Thus, it would be extremely desirable to have available an inexpensive but rugged prosthetic structure permitting users such as carpenters and plumbers to readily kneel and crawl about on their knees.

It is a paramount object of the present invention to provide for a prosthetic device that is rugged but simple in construction and allows the wearer to kneel and move about on the knees on a continuous basis without detrimental effect on the prosthetic device.

It is still another object of the present invention to provide for a prosthetic device that allows the user to rotate the upper and lower leg portions relative to one another between an vertical position representing a leg angle of 180° and a kneeling position representing a leg angle of less than about 30°.

These and other objects will become evident to those skilled in the art following a reading of the description herein and the appended drawings.

SUMMARY OF THE PRESENT INVENTION

The present invention contemplates a prosthesis device for use as an above-knee prosthesis having a first tubular member adapted to support an upper leg prosthesis and a second tubular member spaced from said first member adapted to support a lower leg prosthesis including a foot portion. The first and second members are rotatable relative to one another between a maximum leg angle of about 180° representing an essential erect position of the wearer through a kneeling leg angle of about 60° and a minimum leg angle of about 20°. The first and second members are connected by a connecting arm pivotally connected to the first member and fixedly secured along a lower portion thereof to the second member. The pivot axis of said arm lies between longitudinal axis of said first member and the vertical extension of the contact line between the lower portion and said second member. The connecting arm extends through a continuous slot collectively defined by a cap covering the opening into the lower end of the first member and the adjacent wall of the first member. The connecting arm and slot cooperating to provide a maximum angle of relative rotation between the first and second members but permits a minimum angle of rotation representing a kneeling position.

DETAILED DESCRIPTION OF THE DRAWINGS

DETAILED DESCRIPTION OF THE PREFERRED EMBODIMENT

Figure 1:
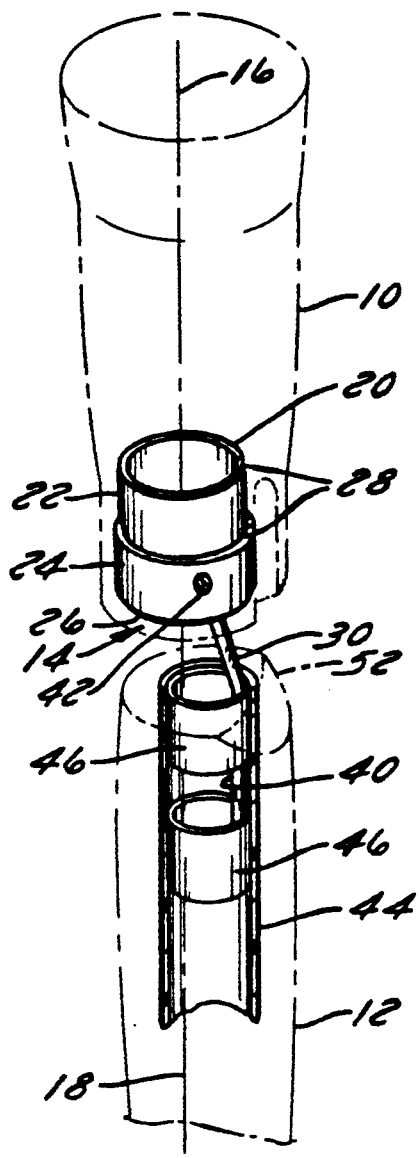
FIG. 1 is a perspective of the prosthetic device of the present invention showing the upper and lower prosthetic members in phantom about respective tubular members with the connecting member connecting the tubular members shown partial in section.
Figure 6:
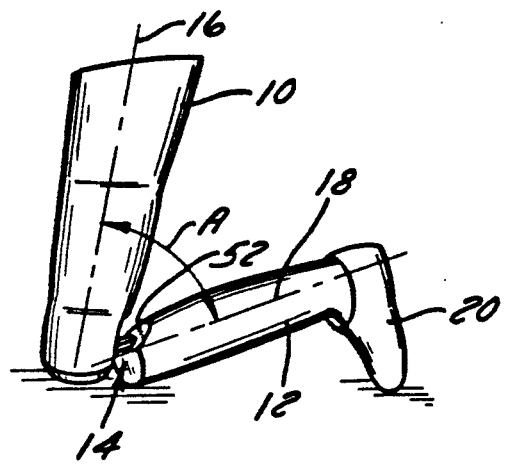
FIG. 6 is a perspective view of the prosthetic device of the present invention showing the device in a kneeling position.
Figure 5:
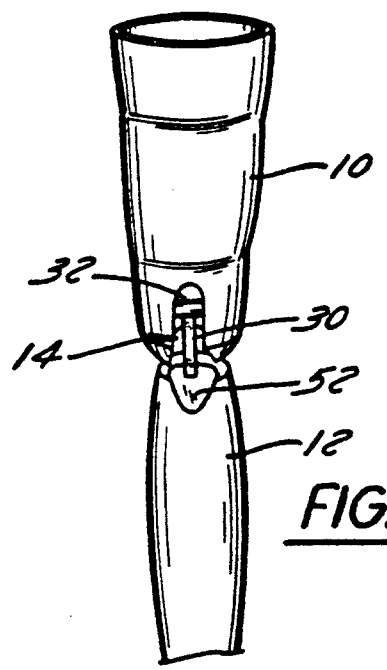
FIG. 5 is a back view in perspective of the prosthetic device of the present invention showing the device in an erect position.

Reference is now made the various Figures, particularly FIGS. 1 and 6, in which are shown an upper leg prosthesis 10 connected to a lower leg prosthesis 12 by a knee joint connecting member shown generally by character numeral 14. In FIG. 1, the entire prosthesis device is in an upright vertical position in which the "leg angle" is 180°. This should be contrasted with the kneeling position shown in FIG. 6 in which the "leg angle" is about 60°. For purposes of this description, the "leg angle" shown by the letter A in FIG. 6 is defined by the intersection of the longitudinal axis 16 passing through the mid point of the upper prosthesis 10 and the longitudinal axis 18 of lower prosthesis 12 which passes essentially through the mid point of foot 20. In the vertical position of FIG. 1, axes 14 and 16 are co-axially aligned.

The knee joint connecting assembly 14 can best be described as having three major sections. The first section comprises a cylindrical member 20 having a tube 22 of a first circumference and a second tube 24 of a second, slightly larger, circumference circumscribing and adhered to the lower portion of tube 22. Alternatively member 20 may be made of a single tube with a thickness of between about $\frac{1}{2}$" to 1".

Figure 2:
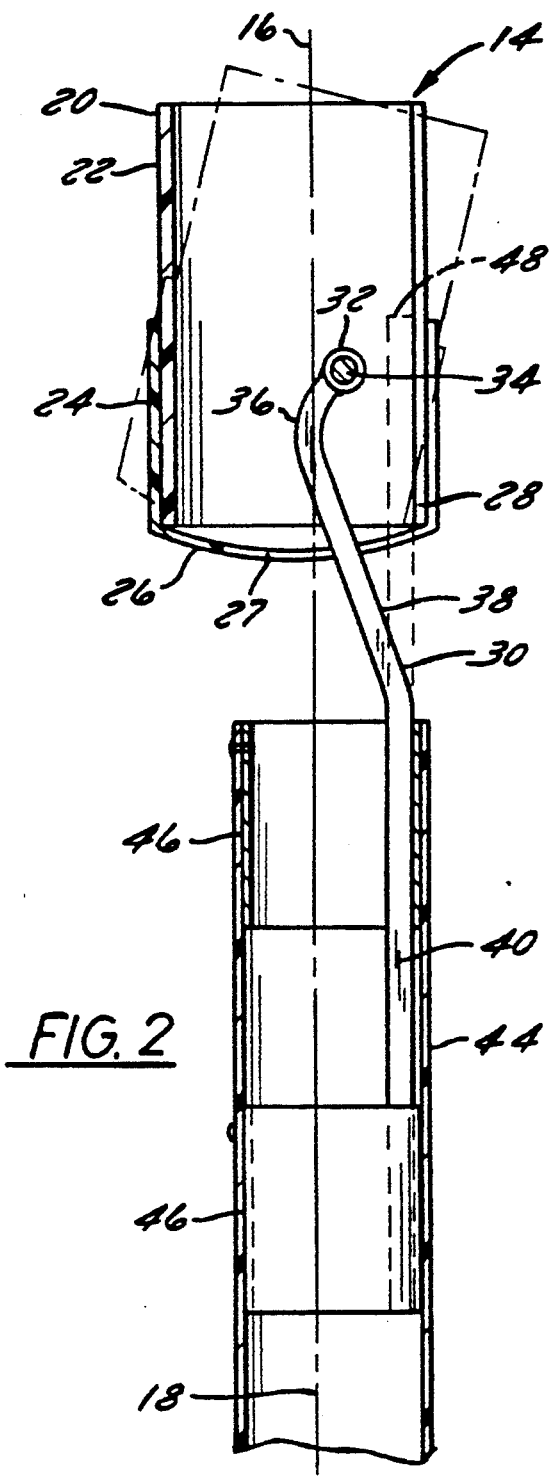
FIG. 2 is a side sectional view of the connecting member of the present invention.
Figure 4:
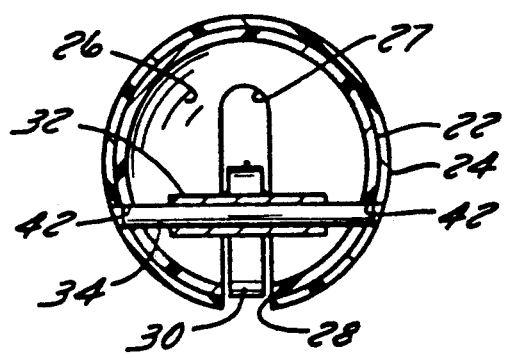
FIG. 4 is a sectional view taken along lines 4—4 of FIG. 3.
Figure 3:
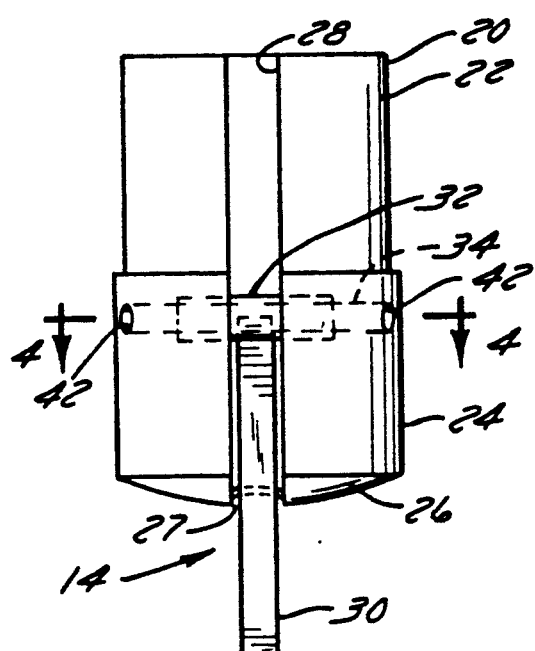
FIG. 3 is a back view of the connecting member of the present invention.

Tubes 22 and 24 are desirably made from a material tough enough to support and maintain the appropriate hinging action of member 14 over a sustained period of time measured in years. It has been determined that polyvinyl chloride tubing having a thickness of about $\frac{1}{2}$" provides a suitable support. The outside diameter dimensions of tube 22 is preferably about-3 $\frac{1}{2}$" with the inside diameter of tube 24 being slightly larger. As best seen in FIGS. 2, 3, and 6, tube 24 is provided with a rounded cap 26, preferably made of essentially the same material, covering the opening into the lower end of tube 24. Cap 26 is provided with a slot 27 extending from the perimeter adjacent slot 28 to a position short of this opposite perimeter (FIG. 4). A vertical slot 28 is defined in the rear wall of tubes 22 and 24 (FIG. 3) and together with slot 27 defines a continuous slot.

For purposes of the description, the upper leg prosthesis and lower leg prosthesis 12 are the external features resembling the contours of the leg. The knee assembly 14 and the upper leg and lower leg prostheses collectively define the "prosthesis device". The prostheses 10 and 12 can be fabricated from any desired light weight filler material such as fiber glass, thermoplastic material or aluminum fitted with a skin having flesh appearance if desired.

As illustrated in FIGS. 2, 3, and 4, a connecting arm 30 is integrally connected to sleeve 32 mounted for rotary movement about hinge pin 34. Hinge pin 34 is mounted in bores 42 within the walls of tubes 22 and 24. The sleeve is sufficiently long to abut the internal surfaces of the tube 22 to prevent any unwanted sliding of pin sleeve 32 along pin 34. It is important to note that the pivot axis of arm 30, i.e. hinge pin 34, is located slightly behind upper longitudinal axis 16. However, arm 30 in this preferred embodiment is provided with a first portion 36 having a convex shape that extends slightly forward of upper axis 16. In this preferred embodiment arm 30 is also provided with a second arm portion 38 that is linear but set at an angle with respect to axis 16. Arm portion 38 extends through the continuous slot defined by slots 27 and 28 to the inside wall of a tube 44 forming part of the third section of knee member 14. A third arm portion 40 is set at an angle with respect to portion 38 permitting it to extend along and abut the inner wall of tube 44. Arm portion 40 is integral with a plurality of mounting rings 46 securely fastened to the wall of tube 44. Each ring has an external diameter complementary to the inside diameter of tube 44 and may be riveted to or fastened in any suitable manner to tube 44. The vertical positioning of rings 46 within tube 44 is preferably such that the upper edge of the top ring 46 is flush with the upper edge of tube 44.

The connecting assembly 14 is preferably constructed of steel with the connecting arm 30 being made from ⅛" steel key stock, for example. The third arm portion 40 may be welded to rings 46 of 12 gauge stainless steel. Similarly, sleeve 32 and hinge pin 34 are also preferably made from compatible steel material. Tube 44 is preferably fabricated from the same material as tubes 22 and 24, namely, polyvinyl chloride.

From FIG. 2, it can be seen that the hinge pin 34 is located between axis 16 and the vertical extension 48 of third arm portion. With a leg angle of about 180°, hinge pin 34 is preferably located almost directly above the mid point of foot 12.

Many manufacturers prefer to sell lower leg prosthesis that are rigidly connected to the foot. If the center of gravity of the wearer is forward of the midpoint of a foot prosthesis, walking on inclines becomes extremely difficult. If, however, the center of gravity acting down through the hinge pin axis is centered over the midpoint, walking on inclines can be easily addressed with only minor adjustments being made between the angle of attachment of the foot to the lower leg prosthesis for individual cases.

As the leg angle is decreased for kneeling such is shown in FIG. 6, the second arm portion 38 moves through the continuous slot defined by slots 27 and 28. The cooperation between portion 38 and the continuous slot allows the user of the prosthesis device to kneel directly on cap 24. The minimum leg angle is constrained only by the eventual contact of upper and lower prosthesis. The upper limit to the leg angle is defined by the abutment of arm portion 38 against the cap wall defining the end of slot 27. A canted surface 52 may be provided on lower leg prosthesis 12 to allow or promote leg angles that may be as small as about 15° to 20°. Additionally, a wearing surface may be provided on the kneeling surface such as cap 24 to resist wear and abrasions that occur in use.

The forward position of curved arm portion 36 causes arm portion 38 to abut the end of slot 28 when the leg angle reaches about 170° to 180°. While this is a preferred upper leg angle limit, it is clear that the forward projection of arm portion 36 and length of slot 28 can be adjusted to provide other upper limits as desired. Additionally, it may be desired in some instances to eliminate the curved portion and allow the linear portion 38 to extend directly to sleeve 32.

Thus, in operation, the prosthesis device of the present invention has a connecting assembly which cooperates with the internal prosthesis support structure, i.e. tubes 22, 24, 44, and various slots therein to permit unimpeded working, and allows the wearer to kneel directly on a surface and to move about in a kneeling position when on a surface. As kneeling occurs, the leg angle decreases and connecting arm 30 moves through the continuous slot and a matching slot in the upper leg prosthesis. Arm 30 in this position no longer extends through cap 26. The cap 26 being rounded acts like a knee cap upon which the user can directly kneel. It should be noted that foot 19 tilts lower leg prosthesis thus requiring the kneeling angle to be less than 90° preferably about 60° as shown in FIG. 6. The lower leg angle is limited only by the contact of the upper and lower prosthesis surfaces which may be about 30° for a lower leg prosthesis without a canted surface. When the prosthesis device is moved back to its vertical position, arm 30 now extends through slot 27 and is connected to spaced lower leg prosthesis 12 as described before. The maximum leg angle is limited by contact of arm 30 with end wall of slot 27.

Thus, from the above it can now be seen that a prosthetic device, simple and rugged in construction, has been devised to allow the wearer to kneel and move about in the kneeling position as desired. Other modifications and changes will be apparent to the skilled worker in this art after a reading of the description and drawings without varying from the scope of the appended claims.

I claim:

1. A leg prosthesis device for permitting a wearer to kneel thereupon comprising a
   (a) a first member adapted to support an upper leg prosthesis;
   (b) a second member spaced from said first member adapted to support a lower leg portion connected to a foot prosthesis;
   (c) said first and second members being movable with respect to each other over a range defined by a maximum leg angle of about 180° and a minimum leg angle of about 20°;
   (d) a connecting member having
      (i) a curved portion pivotally connected at one distal end to said first member and defining a pivot axis between said first and second members,
      (ii) a first linear portion integral with said curved portion and angularly and integrally connected to a second linear portion, and
      (iii) said second linear portion fixedly connected to said second member, said curved portion being pivotably connected to said first member at a point located intermediate a vertical extension of said second linear portion and a vertical axis of said second member when said leg angle is about 180°; and (e) said first member having a slot through which said first linear portion extends and moves therealong having a length defining the limits of said range of leg angles.

2. The prosthesis device of claim 1 in which said first member is a first cylindrically shaped tube and has a cap over the end facing said second member, said slot extending partly through said cap and partly up the side of said tube, the ends of said slot abutting said first linear portion when said first and second members form said maximum and minimum leg angles.

3. The prosthesis device of claim 1 including a pin rigidly mounted across said first member, said curved portion integrally connected to a sleeve rotatably mounted about said pin.

4. The prosthesis device of claim 3 in which the length of said sleeve is approximately equal to an inner diameter of said first member and said curved portion is fixed to the mid point of said first member thereby maintaining centered registry of said connecting member with said first and second members.

5. The prosthesis device of claim 1 in which said first member is a first cylindrically shaped tube and said second member is a second cylindrically shaped tube, said first tube having a pin rigidly mounted therein with said curved member being integrally connected to a sleeve mounted about said pin, said second linear portion being integrally connected to a plurality of annular members positioned inside and secured to said second cylindrically shaped tube.

6. The prosthesis of claim 5 in which said first and second tubes are made from polyvinyl chloride.

7. The prosthetic device of claim 1 in which said first member is tubular and secured to an upper leg prosthesis and said second member is tubular and secured to a lower leg prosthesis connected to a foot prosthesis, aid pivot axis being positioned approximately through a vertical axis passing through the midpoint of said foot prosthesis when said leg angle is about 180° and said upper leg prosthesis pivotable with respect to said lower leg prosthesis about said pivot axis.

8. A prosthetic leg device adapted to allow a wearer to kneel thereupon having
(a) an upper leg prosthesis;
(b) a lower leg prothesis pivotably connected
  (i) to said upper leg prothesis by a connecting member extending form the interior of said upper leg prothesis to the interior of said lower leg prothesis and
  (ii) connected to a foot prosthesis;
(c) a tubular upper member positioned within and fixedly secured to said upper leg prosthesis;
(d) a tubular lower member positioned within and fixedly secured to said lower leg prosthesis;
(e) said connecting member operably connected by an upper portion thereof to said upper tubular member for rotary movement relative thereto and operably secured at a lower portion thereof to said tubular lower member, said upper portion of said connecting member rotating about a sleeve integral with one end of said upper portion and said sleeve rotating about said pin fixed to said upper tubular member, said tubular upper member provided with a cap covering the lower opening of said tubular upper member for kneeling thereupon, said cap together with said upper tubular member and said upper leg prosthesis defining a slot through which said connecting member extends to permit relative rotation of said lower tubular member and lower leg prosthesis over a range defined by a maximum leg angle of about 180° and a minimum leg angle of about 20°, wherein said connecting member has
  (i) said lower portion extending into and fixedly mounted in a parallel relationship with said tubular lower member, said pin having a pivot axis located between the longitudinal axis of said tubular upper member and the longitudinal axis of said lower portion of said connecting member and approximately along a vertical axis extending through the midpoint of said foot prosthesis at a leg angle of about 180° and
  (ii) a curved portion intermediate and integral to said upper portion and lower portion that extends across said longitudinal axes of said upper and lower hollow members when said leg angle is approximately 180°.

9. The device of claim 8 in which said lower portion is integrally mounted to a plurality of annular rings having outer diameters complementary and secured to the inner diameter of said interior member.

10. The prosthetic device of claim 8 in which said upper and lower tubular members are made from polyvinyl chloride.

* * * * *